United States Patent
Wagner et al.

(10) Patent No.: US 7,413,555 B2
(45) Date of Patent: Aug. 19, 2008

(54) JOINT ORTHOSIS

(75) Inventors: Helmut Wagner, Duderstadt (DE); Alexander von Ascheberg, Duderstadt (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 612 days.

(21) Appl. No.: 10/839,699

(22) Filed: May 6, 2004

(65) Prior Publication Data

US 2004/0260220 A1    Dec. 23, 2004

(30) Foreign Application Priority Data

May 9, 2003    (DE)    ................ 103 21 117

(51) Int. Cl.
*A61F 5/00*    (2006.01)
*A61F 5/37*    (2006.01)

(52) U.S. Cl. .............. 602/27; 602/23; 602/26; 128/882

(58) Field of Classification Search ............ 602/23, 602/27, 26, 16; 128/882
See application file for complete search history.

(56) References Cited

U.S. PATENT DOCUMENTS

| | | | |
|---|---|---|---|
| 4,237,873 A | | 12/1980 | Terry et al. |
| 4,508,111 A | | 4/1985 | Hepburn |
| 4,771,768 A | * | 9/1988 | Crispin ............... 602/16 |
| 5,060,640 A | * | 10/1991 | Rasmusson ........... 602/16 |
| RE37,297 E | * | 7/2001 | Smith, III ............ 602/26 |
| 6,500,138 B1 | * | 12/2002 | Irby et al. ............ 602/26 |

| | | |
|---|---|---|
| 2002/0188238 A1 | 12/2002 | Townsend et al. |

FOREIGN PATENT DOCUMENTS

| | | |
|---|---|---|
| DE | 563 009 | 10/1932 |
| DE | 29 18 864 | 11/1980 |
| GB | 750512 | 12/1954 |
| GB | 2 207 457 | 2/1989 |
| GB | 2 235 245 | 2/1991 |

OTHER PUBLICATIONS

European Search Report dated Sep. 1, 2004.

\* cited by examiner

*Primary Examiner*—Patricia Bianco
*Assistant Examiner*—Tarla Patel
(74) *Attorney, Agent, or Firm*—Whitham Curtis Christofferson & Cook, P.C.

(57) ABSTRACT

A joint orthosis with a first joint part (4), a first splint (5) connected to the first joint part (4), a second joint part (1), a second splint (2) connected to the second joint part (1), and a pivot hinge part (3) for articulated connection of the second splint (2) and of the first splint (5), said splints (2, 5) extending into the pivot hinge part (3) from opposite directions and laterally offset relative to one another, being arranged with their ends next to one another in the pivot hinge part (3), and being able to pivot to a small extent relative to one another, can be configured with a lower overall height by virtue of the fact that the pivot hinge part (3) has two chambers (8, 10) which are arranged substantially parallel and are laterally offset relative to one another and which are open in opposite directions, and into which the ends of the splints (2, 5) extend, and by virtue of the fact that the second splint (2) is mounted in the end area of its chamber (10) so as to be able to pivot about a pivot axis (D) in such a way that the pivoting movement of the second splint (2) relative to the pivot hinge part (3) is limited by the chamber (10).

7 Claims, 1 Drawing Sheet

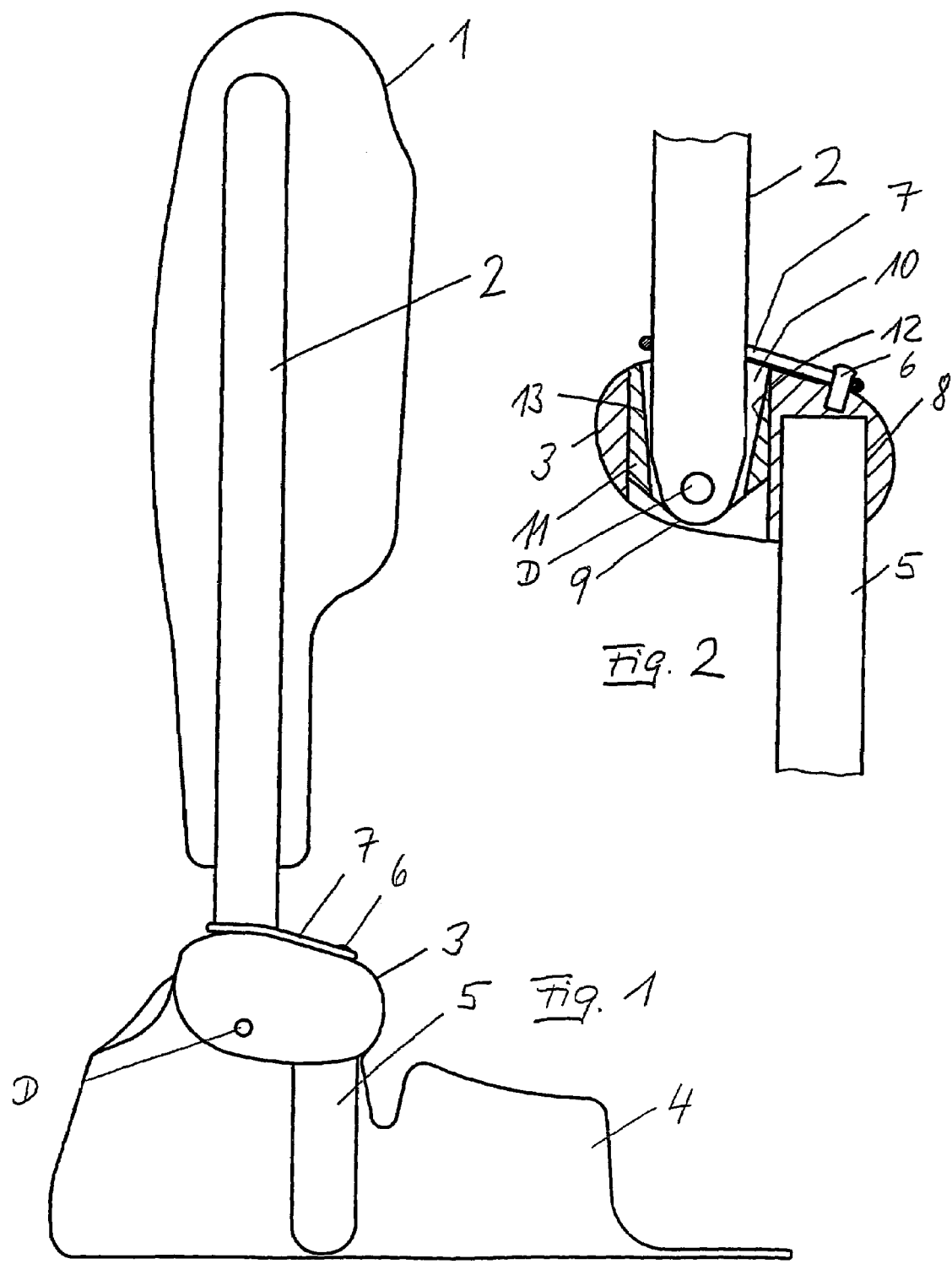

JOINT ORTHOSIS

FIELD OF THE INVENTION

The invention relates to a joint orthosis with a first joint part, a first splint connected to the first joint part, a second joint part, a second splint connected to the second joint part, and a pivot hinge part for articulated connection of the second splint and of the first splint, said splints extending into the pivot hinge part from opposite directions and laterally offset relative to one another, being arranged with their ends next to one another in the pivot hinge part, and being able to pivot to a small extent relative to one another.

Joint orthoses of this type are used in particular as ankle joint orthoses to assist walking and standing in a person handicapped in the lower leg and foot region. The pivot hinge part in this case permits a relatively small pivoting movement of the first joint part relative to the second joint part.

BACKGROUND

In the known orthoses of this type, the two splints are oriented flush with one another and are designed to be able to pivot relative to one another about a common pivot axis, the pivot hinge part having to be provided with a means of limiting the relative pivoting movement. In an ankle joint orthosis, a foot-elevating function can be effected by means of the foot part being pressed by a spring into a starting position which, through the pressure applied when putting down the heel of the foot part (first joint part) counter to the spring force, is abandoned in order to thus permit a certain heel-to-toe rolling movement during walking.

The foot part and the below-knee part (second joint part) are generally designed as shells made of plastic in order to engage in a supportive manner in a U-shape around the foot and the lower leg. For stable connection of the foot splint and of the foot part, a certain length is required which, in the known construction, has to be provided below the pivot hinge part. In addition, a certain length is needed for the anchoring of the foot splint in the pivot hinge part. For this reason, a certain minimum structural height is needed for the foot part up to the pivot hinge axis. For kinematic and esthetic reasons, however, it would be advantageous to permit a design of the foot part with a lower height.

DE 563 009 discloses a joint orthosis of the type mentioned at the outset, in which a sole part engaging under the foot of the prosthesis wearer is connected to an upwardly extending lateral splint consisting of two parts which are connected to one another by a hinge. The hinge part comprises, on both sides, the upper end of the lower splint part and the lower end of the upper splint part, the lower end of the upper splint part being mounted pivotably on the hinge part. The upper end of the lower splint part extends upward beyond the hinge part so as to limit the pivoting movement of the upper joint part toward the front, in other words to define the extended position of the lateral splint. The hinge part is arranged in this case at a substantial distance from the sole part, so as to lie safely above the upper edge of the shoe during use. The limit stop formed by the upper end of the lower splint is adjustable by means of leather or metal tongues of greater or lesser thickness or, if appropriate, a displaceable wedge being inserted between the splints.

GB 2 235 245 A discloses a polycentric knee joint consisting of two pivot hinges which, in the extended state, are flush with one another and are formed in a hinge housing. The hinge housing delimits the maximum extension of the joint splints with the aid of a T-shaped insert between the side walls of the hinge housing. By means of different inserts, it is possible to form different extension angles which can deviate to a greater or lesser extent from 180°.

SUMMARY

It is an object of the invention to design a joint orthosis of the type mentioned at the outset in such a way that a hinge part can be given a low overall height.

To achieve this object, the invention proposes a joint orthosis of the type mentioned at the outset which is characterized by the fact that the pivot hinge part has two chambers which are arranged substantially parallel and are laterally offset relative to one another and which are open in opposite directions, and into which the ends of the splints extend, and by the fact that the second splint is mounted in the end area of its chamber so as to be able to pivot about a pivot axis in such a way that the pivoting movement of the second splint relative to the pivot hinge part is limited by the chamber.

In the joint orthosis according to the invention, the pivot hinge part thus has two chambers which are oriented substantially parallel to one another, wherein one splint can be inserted fixedly into its (downwardly open) chamber, while the other splint is inserted into the rearwardly offset and preferably upwardly open chamber so as to be able to pivot about a certain angle. The pivot axis is situated in the end area of the chamber pivotably receiving the splint.

The lengths required for the function of the two chambers are thus established next to one another in the pivot hinge part and not, as was previously the case, in the direction of the splints oriented flush with one another, with the result that a length of the chambers in the construction height of the joint orthosis according to the invention can be saved. In an ankle joint orthosis, there is a favorable introduction of force into the foot part by virtue of the fact that the foot splint is offset to the front in the foot direction in relation to the below-knee splint, and more to the center of the foot, and thus corresponds better to the natural conditions.

In addition, the joint orthosis according to the invention permits a very simple but stable construction by virtue of the fact that an insert part which laterally guides the splint and has limit stops for the pivoting movement of the splint is inserted into the chamber of the pivotably mounted splint. The lateral guiding means and the limit stops can thus be made of a plastic material suitable for this purpose, for example PTFE, although the splints and the pivot hinge part are preferably made of metal.

If, in a particularly preferred embodiment of the invention, the insert part is inserted exchangeably into the pivot hinge part, it is possible, by simply changing the insert part, to adapt the orthosis to the particular patient, thereby defining the angle setting for the starting position and the maximum relative pivot angle between below-knee splint and foot splint.

In one very simple form, in an ankle joint orthosis it is also possible to create a foot-elevating function by means of a spring, preferably a tensioned resilient rubber band which, at one end, is run round the below-knee splint and, at the other end, round a mushroom-shaped securing knob on the top face of the pivot hinge part.

The invention is explained in more detail below with reference to an illustrative embodiment shown in the drawing, in which:

DESCRIPTION OF THE DRAWINGS

FIG. 1 shows a side view of an illustrative embodiment of a joint orthosis according to the invention designed as an ankle joint orthosis, FIG. 2 shows a cross section through the pivot hinge part provided in this embodiment.

DETAILED DESCRIPTION

The view in FIG. 1 reveals a shell-like, supportive below-knee part (second joint part) 1 which is open to the front, that is to say engages laterally round the lower leg in the calf area. At one side, the below-knee part 1 is connected firmly to a below-knee splint (second splint) 2. The below-knee splint 2 extends into a pivot hinge part 3 and is mounted pivotably in the pivot hinge part 3 by means of a pivot axis D. Offset laterally and to the front, a foot splint (first splint) 5 extends from underneath into the pivot hinge part 3 and is connected to a shell-shaped foot part (first joint part) 4 open to the top and to the front. The foot splint 5 is inserted fixedly into the pivot hinge part 3, i.e. is laterally immovable.

On its top face, the pivot hinge part 3 has a mushroom-shaped securing knob 6 around which a resilient rubber band 7 runs, the other end of which is run round the below-knee splint 2.

The cross-sectional view in FIG. 2 illustrates that the foot splint 5 is inserted with matching fit into a downwardly open chamber 8 of the pivot hinge part 3 so that the foot splint 5 is immovable in the pivot hinge part 3.

By contrast, the below-knee splint 2 extends with a front, slightly tapered and rounded end 9 into an upwardly open chamber 10 of the pivot hinge part 3. In the chamber there is an exchangeable insert part 11 made of a suitable plastic with good slide properties, for example PTFE. The insert part 11 guides the below-knee splint 2 laterally, for executing the pivoting movement about the pivot axis D, and, with a front limit stop edge 12 and a rear limit stop edge 13, sets the angles for the end positions of the pivoting movement of the below-knee splint 2 relative to the pivot hinge part 3, and thus to the foot splint 5. Thus, by exchanging the insert part 11, the angle setting in the standing position and the pivot angle range of the below-knee splint 2 relative to the foot splint 5 for the respective patient can be suitably set while the other structural parts remain unchanged. By means of the prestressed resilient rubber band 7, the foot part 4 in the unloaded position is drawn upward to the maximum extent relative to the below-knee part 1, which corresponds to a foot-elevating function. When putting the foot part 4 down on the heel area, the lever effect of the foot part 4 means that the resilient rubber band 7 is stretched, so that the foot part 4 assumes a greater angle relative to the below-knee part 1, in order to permit a certain heel-to-toe rolling of the foot part 4 relative to the below-knee part 1 during walking.

FIG. 2 shows in particular that the pivot axis D can be arranged in the lower area of the pivot hinge part 3, and that the foot splint 5 can be inserted in a stable manner into a chamber 8 extending as far as the upper area of the pivot hinge part 3, by which means the structural height of the foot part 4 can be reduced significantly up to the pivot axis D, without having to accept compromises in respect of the stability of the anchorage in the pivot hinge part 3.

It will be readily appreciated that the illustrative embodiment shown in the drawing can be configured, with suitable adaptation, also as a whole-leg orthosis.

The invention claimed is:

1. A joint orthosis, comprising:
   a first joint part;
   a first splint connected to the first joint part;
   a second joint part;
   a second splint connected to the second joint part; and
   a pivot hinge part for articulated connection of the second splint and the first splint, said first and second splints extending into the pivot hinge part from opposite directions and being laterally offset relative to one another, said first and second splints being arranged with ends of said first and second splints next to one another in the pivot hinge part, and said first and second splints being able to pivot relative to one another around one pivot axis,
   wherein the pivot hinge part has two chambers which are arranged substantially parallel and are laterally offset relative to one another and which are open in opposite directions, and into which the ends of the first and second splints extend, and
   wherein the second splint is mounted in an end area of one of said two chambers so as to be able to pivot about a pivot axis in such a way that the pivoting movement of the second splint relative to the pivot hinge part is limited by said one of said two chambers.

2. The joint orthosis as claimed in claim 1, wherein the first splint is inserted fixedly into one of said two chambers.

3. The joint orthosis as claimed in claim 1, wherein an insert part is inserted into one of said to chambers in which the second splint is inserted, which insert part laterally guides the second splint and has limit stops for the pivoting movement of the second splint.

4. The joint orthosis as claimed in claim 3, wherein the insert part is inserted exchangeably into the pivot hinge part.

5. The joint orthosis as claimed in claim 3, wherein the second splint is pressed by a spring against one of the limit stops of the insert part.

6. The joint orthosis as claimed in claim 5, wherein said spring is a tensioned resilient rubber band, and further comprising a mushroom-shaped securing knob arranged on a top face of the pivot hinge part, said mushroom-shaped securing knob is looped by said tensioned resilient rubber band surrounding the second splint.

7. The joint orthosis as claimed in claim 1, wherein a foot part is associated with said first joint part and a below-knee part is associated with said second joint part.

* * * * *